(12) United States Patent
Cockerell

(10) Patent No.: US 9,351,913 B2
(45) Date of Patent: *May 31, 2016

(54) SPF LIQUID CLEANSING COMPOSITIONS AND METHODS OF USE

(71) Applicant: Cockerell Dermatology Development, Ltd., Dallas, TX (US)

(72) Inventor: Clay J. Cockerell, Dallas, TX (US)

(73) Assignee: Cockerell Dermatology Development, Ltd., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,787

(22) Filed: Nov. 2, 2014

(65) Prior Publication Data

US 2015/0059792 A1      Mar. 5, 2015

Related U.S. Application Data

(63) Continuation of application No. 12/344,042, filed on Dec. 24, 2008, now Pat. No. 8,877,166.

(60) Provisional application No. 61/136,916, filed on Oct. 14, 2008.

(51) Int. Cl.

| | | |
|---|---|---|
| *A61Q 17/04* | (2006.01) |
| *A61K 8/49* | (2006.01) |
| *A61K 8/27* | (2006.01) |
| *A61K 8/29* | (2006.01) |
| *A61K 8/31* | (2006.01) |
| *A61K 8/40* | (2006.01) |
| *A61K 8/58* | (2006.01) |
| *A61Q 19/10* | (2006.01) |
| *A61K 8/02* | (2006.01) |
| *A61K 8/22* | (2006.01) |
| *A61K 8/46* | (2006.01) |

(52) U.S. Cl.
CPC .............. *A61K 8/492* (2013.01); *A61K 8/0245* (2013.01); *A61K 8/22* (2013.01); *A61K 8/27* (2013.01); *A61K 8/29* (2013.01); *A61K 8/31* (2013.01); *A61K 8/40* (2013.01); *A61K 8/463* (2013.01); *A61K 8/585* (2013.01); *A61Q 17/04* (2013.01); *A61Q 19/10* (2013.01); *A61K 2800/612* (2013.01); *A61K 2800/651* (2013.01); *A61K 2800/74* (2013.01)

(58) Field of Classification Search
None
See application file for complete search history.

(56) References Cited

U.S. PATENT DOCUMENTS

2004/0161395 A1*   8/2004   Patil .................. A61K 8/891
                                                        424/70.12

\* cited by examiner

*Primary Examiner* — Abigail Fisher
*Assistant Examiner* — Jessica Kassa
(74) *Attorney, Agent, or Firm* — Winstead PC

(57) ABSTRACT

The present application relates to a facial and/or body wash composition that after rinsing provides a sun protection factor of at least about 6 comprising (i) red petrolatum; (ii) at least one surface-treated metal oxide pigment that blocks ultraviolet radiation in the wavelength range of from about 290 nm to about 400 nm; (iii) at least one organic sunscreen agent having a log P of greater than about 4.0 that blocks or absorbs ultraviolet radiation in the wavelength range of from about 290 nm to about 400 nm; (iv) at least one lathering anionic surfactant; (v) at least one lathering non-ionic surfactant; (vi) an alkyl silicone; and (vii) a volatile cyclic silicone.

9 Claims, No Drawings

SPF LIQUID CLEANSING COMPOSITIONS AND METHODS OF USE

CROSS REFERENCE TO RELATED APPLICATIONS

This Application is a continuation of application Ser, No. 12/344,042 filed Dec. 24, 2008, now U.S. Pat. No. 8,877,166, which claims the benefit under 35 U.S.C. §119(e) of U.S. Provisional Patent Application No. 61/136,916 filed Oct. 14, 2008, which is incorporated herein by reference in its entirety as if fully set forth herein.

FIELD OF INVENTION

The present invention relates to liquid skin cleansing compositions which, after rinsing, deposit on a substrate (e.g., skin or hair) a film that blocks or attenuates ultraviolet radiation.

Four related patents assigned to Aquea Scientific—U.S. Pat. Nos. 6,998,113; 7,001,592; 7,025,952; 7,037,513—describe a body wash and body wash additive in which a sunscreen is encapsulated in sol-gel microcapsules. After application of the body wash to the skin (e.g., in a shower) and rinsing, the patents claim to protect the skin from ultraviolet radiation. These patents as well as other patents and published patent applications referenced hereinbelow are, to the extent pertinent, incorporated herein in their entirety.

The use of melanin or a melanin precursor selected from the group consisting of L-dopa, tyrosine, tryptophan, and cysteine in a personal care product that provides SPF is described in U.S. Pat. Nos. 4,855,144 and 4,806,360.

SUMMARY OF THE INVENTION

The present application relates to a facial and/or body wash composition that after rinsing provides a sun protection factor ("SPF") of at least about 6 comprising:
(a) red petrolatum;
(b) at least one surface-treated metal oxide pigment that blocks ultraviolet radiation in the wavelength range of from about 290 nm to about 400 nm;
(c) at least one organic sunscreen agent having a log P of greater than about 4.0 that blocks or absorbs ultraviolet radiation in the wavelength range of from about 290 nm to about 400 nm;
(d) at least one lathering anionic surfactant;
(e) at least one lathering non-ionic surfactant;
(f) an alkyl silicone; and
(g) a volatile cyclic silicone.

DETAILED DESCRIPTION OF THE INVENTION

The present application relates to a liquid skin cleaning composition that after rinsing leaves a deposit on a substrate and thereby provides protection from ultraviolet radiation, expressed as SPF, of at least about 6 comprising:
(a) red petrolatum;
(b) at least one surface-treated metal oxide pigment that blocks ultraviolet radiation in the wavelength range of from about 290 nm to about 400 nm;
(c) at least one organic sunscreen agent that having a log P of greater than about 4.0 that blocks or absorbs ultraviolet radiation in the wavelength range of from about 290 nm to about 400 nm;
(d) at least one lathering anionic surfactant;
(e) at least one lathering non-ionic surfactant;
(f) an alkyl silicone; and
(g) a volatile cyclic silicone.

Surface-treated metal oxide pigments that block ultraviolet radiation in the wavelength range of from about 290 nm to about 400 nm suitable for use in the present invention include, but are not limited to, the following: micronized zinc oxide surface-treated with an alkoxysilane; micronized titanium dioxide surface-treated with alkoxysilane; micronized titanium dioxide surface-treated with silica, alumina and dimethicone/methicone copolymer; micronized titanium dioxide surface-treated with alumina and dimethicone/methicone copolymer; micronized zinc oxide surface-treated with an alkoxycaprylylsilane; and micronized titanium dioxide surface-treated with an alkoxycaprylylsilane.

A particularly preferred micronized titanium dioxide pigment that is surface-treated with an alkoxycaprylylsilane is titanium dioxide coated with trimethoxycaprylylsilane, available from Degussa under the tradename TEGO Sun T 805.

In a preferred embodiment, the SPF liquid skin cleansing composition of the present invention comprises titanium dioxide coated with trimethoxycaprylyl-silane at a concentration of from about 1.0% to about 5% based on the total weight of the composition. (Unless otherwise noted, where the concentration of an individual ingredient is expressed as a percentage, the percentage is to be understood as the percentage by weight of the ingredient based on the weight of the total composition.) More preferably, the titanium dioxide coated with trimethoxycaprylylsilane is present in compositions of the present invention at a concentration of from about 1.5% to about 2.5%.

A particularly preferred micronized zinc oxide pigment that is surface-treated with an alkoxycaprylylsilane is zinc oxide coated with triethoxycaprylylsilane, available from BASF under the tradename Z-Cote HP1.

In a preferred embodiment, the SPF liquid skin cleansing composition of the present invention comprises zinc oxide coated with triethoxycaprylylsilane at a concentration of from about 5% to about 10%. More preferably, the zinc oxide coated with triethoxycaprylylsilane is present at a concentration of from about 7.5% to about 8.5%

Other alkoxysilane coated inorganic pigments that block ultraviolet radiation in the wavelength range of from about 290 nm to about 400 nm are described in U.S. Pat. Nos. 5,223,250, 5,536,492 and 5,556,591.

In a particularly preferred embodiment, the SPF liquid skin cleansing composition of the present invention comprises two surface-treated metal oxide pigments that block ultraviolet radiation in the wavelength range of from about 290 nm to about 400 nm. More preferably, the two surface-treated metal oxide pigments are present at a combined concentration (based on the total weight of the composition) of at least about 8.5%.

The at least one organic sunscreen agent having a log P of greater than about 4 that blocks or absorbs ultraviolet radiation in the wavelength range of from about 290 nm to about 400 nm includes sunscreens currently approved by the FDA and listed in the Sunscreen Drug Products for Over-The-Counter Human Use Final Monograph published in the Federal Register on May 21, 1999 at Volume 64, Number 98, pages 27666-27693 as well as organic sunscreen agents approved by regulatory agencies in countries other than the United States.

Log P is a term known to those of skill in the chemical arts. It is a measure of differential solubility of a compound in two solvents. More particularly, it is a partition coefficient expressed as the log ratio of the concentrations of the solute in the solvent.

(A partition coefficient well known to persons having ordinary skill in the art is based on the solvents Octanol and Water.)

In a preferred embodiment, the at least one organic sunscreen agent having a log P of greater than about 4.0 that blocks or absorbs ultraviolet radiation in the wavelength range of from about 290 um to about 400 nm is selected from the group consisting of octylmethoxycinnamate, octocrylene and octyl salicylate.

A particularly preferred organic sunscreen agent having a log P of greater than about 4.0 that blocks or absorbs ultraviolet radiation in the wavelength range of from about 290 nm to about 400 nm is octocrylene, a cyano-diphenylacrylate.

The SPF liquid skin cleansing compositions of the present invention contain at least two lathering surfactants, one anionic and one non-ionic.

By "lathering surfactant" is meant a surfactant having a log P of less than about 2.5 that produces foam when mixed with and agitated in water. Without wishing to be bound by a theory, it is believed that surfactants having a log P of greater than 2.5 impede deposition of sunscreens and sun-blocking agents (i.e., metal oxide pigment that blocks ultraviolet radiation) after rinsing.

In a particularly preferred embodiment, the anionic lathering surfactant is a sulfate.

Preferred sulfates suitable for use in compositions of the present invention are alkyl sulfates and alkyl ether sulfates. Two particularly preferred sulfates are sodium laureth sulfate and ammonium laureth sulfate.

Sodium laureth sulfate is an article of commerce available from a number of sources, including under the tradename Steol CS-370 from Stepan. It has a molecular formula $CH_3(CH_2)_{10}CH_2(OCH_2CH_2)_2OSO_3Na$ and conforms to the following structure:

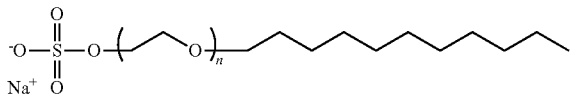

Preferably, the SPF liquid skin cleansing composition of the present invention comprises sodium laureth sulfate a concentration of from about 10% to about 15%.

In a preferred embodiment, ammonium laureth sulfate is used in combination with an alkyl glucoside, preferably decyl glucoside. The combination of ammonium laureth sulfate and decyl glucoside is sold under the tradename Plantaren PS-100 by Cognis. Preferably, ammonium laureth sulfate in combination with decyl glucoside is present in compositions of the present invention at a concentration of from about 5% to about 10%, more preferably from about 7.5% to about 8.5%.

In an especially preferred embodiment the SPF liquid skin cleansing composition of the present invention comprises two anionic lathering surfactants, preferably two sulfates. Still more preferably, the first sulfate is a sodium laureth sulfate and the second sulfate is ammonium laureth sulfate in combination with decyl glucoside. In this especially preferred embodiment, the two sulfates are present at a combined concentration of from about 15% to about 25%.

A preferred class of non-ionic surfactants having a log P of less than about 2.5 suitable for use in the SPF liquid cleansing compositions of the present invention is alkoxylated alcohols.

A preferred class of alkoxylated alcohols is polyoxyethylene alkyl ethers. A particularly preferred polyoxyethylene alkyl ether is the polyethylene glycol ether of stearyl alcohol conforming to the structure:

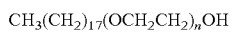

where n has an average value of 21.

Known as Steareth-21 under the International Nomenclature of Cosmetic Ingredients (INCI) naming convention administered by the Personal Care Products Council (formerly the Cosmetic Toiletry and Fragrance Association), polyoxyethylene stearyl ether is commercially available from a number of sources including Uniqema (New Castle, Del.) under the tradename Brij 721.

The SPF liquid skin cleansing compositions of the present invention may comprise one or more additional surfactants selected from the group consisting of sarcosinates, isethionates and taurates. Sarcosinates, isethionates and taurates are well-known to persons having ordinary skill in the art and include those disclosed in U.S. Pat. No. 7,115,551, McCutcheon's Detergents and Emulsifiers (1986) and McCutcheon's Functional Materials (1992), the disclosures of which are incorporated herein by reference.

One preferred additional surfactant is sodium lauroylsarcosine. In one embodiment of the present invention, in addition to the anionic and non-ionic lathering surfactants disclosed in the preceding paragraphs, sodium lauroylsarcosine is present at a concentration of from about 4% to about 8%. Sodium lauroylsarcosine is available under the tradename Crodasinic LS95 from Croda.

Compositions of the present invention may also include acrylate salts. One preferred acrylate salt suitable for use in the SPF liquid cleansing compositions of the present invention is sodium acrylates in combination with caprylic triglyceride. This combination, available commercially from BASF under the tradename Luvigel EM, is preferably used in compositions of the present invention at a concentration of from about 1% to about 5%.

Red petrolatum is an essential element of the present invention. It is an article of commerce available from a variety of suppliers, including Penreco. In preferred embodiments of the present invention, red petrolatum is present at a concentration of from about 4% to about 10%, more preferably from about 7% to about 9%.

SPF liquid cleansing compositions of the present invention also comprise an alkyl silicone, also known in the art as a silicone wax, preferably at a concentration of from about 0.5% to about 3.0%.

One preferred alkyl silicone is $C_{30}$-$C_{45}$ alkyl methicone and $C_{30}$-$C_{45}$ olefin available from Dow Corning under the tradename AMS-C30 Cosmetic Wax. This alkyl silicone conforms to the formula:

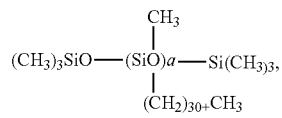

Preferably, $C_{30}$-$C_{45}$ alkyl methicone and $C_{30}$-$C_{45}$ olefin is present at a concentration of from about 0.5% to about 1.5%.

Another preferred alkyl silicone is phenyl isopropyl dimethicone, available under the tradename Silwax DO-MS from Siltech Corp. (Toronto, Ontario, Canada). Phenyl isopropyl dimethicone is polydimethylsiloxane with methyl styrene groups attached soluble in both mineral oil and cyclosiloxane has viscosity of 100 centistokes at 25° C.

Yet another preferred alkyl silicone suitable for use in the SPF liquid cleansing compositions of the present invention conforms to the following structure:

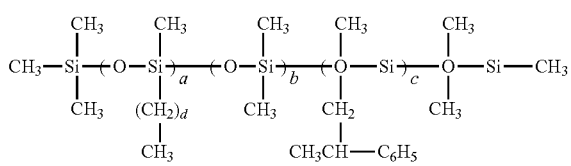

wherein
a is an integer ranging from 1 to 20;
b is an integer ranging from 1 to 20;
c is an integer ranging from 1 to 20;
d is an integer ranging from 7 to 17; and
the ratio of a to c is from about 0.75 to about 1.5.

The SPF liquid cleansing compositions of the present invention also comprise a cyclic volatile silicone conforming to the formula:

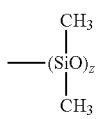

wherein z is an integer from 3 to 6.

Volatile cyclic silicones are articles of commerce available from a number of suppliers including Dow Coming Corporation, General Electric and Shinetsu. The term "volatile" means that the silicone has a measurable vapor pressure. Among the volatile cyclic silicones is cyclopentasiloxane.

A preferred volatile cyclic silicone is polydimethylcyclosiloxane composed mainly of cyclopentasiloaxane having a heat of vaporization (measured at 25° C.) of about 157 kJ/kg. This volatile cyclic silicone is commercially available under the tradename Dow Coming 245 Fluid from Dow Corning.

Optionally, the SPF liquid cleansing compositions of the present invention comprises melanin or a melanin precursor selected from the group consisting of L-dopa, tyrosine, tryptophan, and cysteine. The melanin or melanin precursor is present in a concentration of from about 0.1% to about 20%, preferably from about 0.2% to about 10%. The melanin or melanin precursor may be in a suitable solution or in an encapsulated form as described in U.S. Pat. Nos. 4,855,144 and 4,806,360.

Optionally, the SPF liquid cleansing compositions of the present invention comprises iron oxide pigments (e.g., yellow, red, black). The surfaces of the iron oxide pigment may be treated with a coating sufficient to render them water repellant (i.e., hydrophobic) or oil dispersible (i.e., lipophilic). Coated iron oxide pigments suitable for use in the present invention and the process for making them are described in U.S. Pat. No. 5,143,722, particularly at Col. 2, line 43-Col. 3, line 62.

In one aspect of the present invention, the SPF liquid cleansing composition is aerosolized. Embodiments according to this aspect of the invention are comprised of
(a) an SPF liquid cleansing concentrate comprised of
   (i) red petrolatum;
   (ii) at least one surface-treated metal oxide pigment that blocks ultraviolet radiation in the wavelength range of from about 290 nm to about 400 nm;
   (iii) at least one organic sunscreen agent that having a log P of greater than about 4.0 that blocks or absorbs ultraviolet radiation in the wavelength range of from about 290 nm to about 400 nm;
   (iv) at least one lathering anionic surfactant;
   (v) at least one lathering non-ionic surfactant;
   (vi) an alkyl silicone; and
   (vii) a volatile cyclic silicone; and
(b) a liquefied hydrocarbon propellant suitable for application to human skin selected from the group consisting of butane, isobutane, propane, pentane, and mixtures thereof.

In a preferred aspect of this embodiment of the invention, the propellant is a mixture of isobutane, butane and propane, known in the art as A46. The following blends of isobutane, butane and propane are also suitable for use in the present invention: AP30 (11% Propane, 29% Isobutane, 60% n-butane); AP40 (22% Propane, 24% Isobutane, 54% n-butane); and AP70 (31% Propane, 23% Isobutane, 46% n-butane).

Containers that are suitable for storing and dispensing aerosolized SPF liquid cleansing products are well known in the art and are typically comprised of a metal container body, a valve and an actuator or button. The container body and valve are made of materials compatible with the essential (and optional) chemical ingredients of the compositions of the present invention. Preferably, the container body is preferably made of aluminum. More preferably, the interior surface of the container body is coated with an inert material. Still more preferably, the interior surface of an aluminum can is coated with an epoxy.

In a preferred aspect of the present invention, 94%-97% of the concentrate is added to an aluminum container. Thereafter 3% to 6% of A-46 propellant is charged into the container at a pressure of 46 psig, +/−8 psig.

During storage, transport and distribution, the temperature of aerosolized SPF liquid cleansing composition may rise to around 50° C. Accordingly, the filled aerosol container (i.e., concentrate charged with propellant) is immersed in a hot water bath for sufficient time to allow the contents to reach the internal pressure that would be achieved if the aerosol was allowed to equilibrate at a temperature of from about 50° C. to 55° C. Typically, the equilibration is accomplished after two to three minutes of immersion.

The compositions of the present invention, including aerosolized embodiments, may contain one or more of the following personal care ingredients commonly-used in cleansing compositions: rheology modifiers, pH modifiers, moisturizers, humectants, emollients (e.g., caprylic/capric triglycerides), structuring agents (e.g., beeswax, candelilla wax, paraffin), stabilizers, lubricants, fragrances, preservatives, or coloring agents, including those listed in the following U.S. patents, each of which is incorporated, to the extent pertinent, in its entirety by reference: U.S. Pat. Nos. 4,015,009; 4,024,106; 4,455,295; 4,613,499; 4,710,373; 4,863,963; 5,160,731; 5,338,539; 5,426,210; 5,783,173; and 5,917,088.

Another aspect of the present invention is directed to an all-in-one multifunctional, moisturizing cleanser that both provides SPF and imparts color to the skin after application, washing, rinsing and drying. Cleansing compositions according to this aspect of the invention are comprised of iron oxide pigments as well as red petrolatum, at least one, preferably two, anionic lathering surfactants, a non-ionic lathering surfactant, surface-treated zinc oxide pigments, surface-treated titanium dioxide pigments, an organic sunscreen having a log P of at least about 4.0, an alkyl silicone and a volatile cyclic silicone, each at the concentrations set out above.

It is an object of the present invention to leave a residual deposit on a substrate after rinsing that provides a certain minimum protection from ultraviolet radiation. Accordingly, one aspect of the present invention is directed to a cleansing composition that after rinsing leaves a residual deposit on a substrate to provide an SPF of at least about 6. SPF after rinsing is measured according to the method described in Example 2 below.

While cleansing compositions of the present invention may leave a residual deposit after rinsing that provides a desired SPF on a variety of non-living surfaces, including natural and synthetic fabrics, woven and non-woven, plastics and wood, a preferred aspect of the present invention is directed to leaving a desired SPF after rinsing on human or mammalian skin or hair.

The following examples are further illustrative of the present invention.

The components and specific ingredients are presented as being typical, and various modifications can be derived in view of the foregoing disclosure within the scope of the invention.

EXAMPLE 1

Body Wash with SPF 8 After Rinsing

| Part A (Surfactant Phase) | | |
| --- | --- | --- |
| Sodium Laureth Sulfate (Steol CS-370, Stepan) | 11.40 | 10.0-15.0 |
| Polyoxyethylene Stearyl Ether (Brij 721, Uniqema) | 6.50 | 5.0-8.0 |
| Decyl Glucoside and Ammonium Laureth Sulfate (Plantaren PS-100, Cognis) | 8.30 | 5.0-10.0 |
| Sodium Lauroylsarcosine (Crodasinic LS95) | 3.00 | 1.0-5.0 |
| Caprylic Triglycerides and Sodium Acrylates (Luvigel EM, BASF) | 5.90 | 4.0-8.0 |
| Melanin | 2.00 | 1.5-3.0 |
| Hydroxyethyl Cellulose (Natrosol 250HHR CS, Hercules) | 0.75 | 0.50-1.25 |
| Deionized water | qs to 100 | |
| Part B (Sunscreens) | | |
| O—$TiO_2$ (Z-Cote HP1, BASF) | 1.61 | 1.0-5.0 |
| O—ZnO (Tego Sun T 805 G, Degussa) | 7.90 | 5.0-10.0 |
| Octocrylene (Uvinul N 539 T, BASF) | 4.08 | 2.0-7.0 |
| Red Petrolatum (Tech. Grade, Penreco) | 7.90 | 4.0-10.0 |
| $C_{30-45}$ alkyl methicone and $C_{30-45}$ olefin (Cosmetic Wax AMS-C30, Dow Corning) | 1.00 | 0.5-3.0 |
| Decamethylcyclopentasiloxane (245 Silicone Fluid, Dow Corning) | 4.37 | 2.0-7.0 |
| Part C (Preservative, Fragrance) | | |
| Methylchloroisothiazolinone and Methylisothiazolinone (Kathon CG, Rohm & Haas) | 0.01 | 0.005-0.05 |
| Aromatic Essential Oil of Lilac | 0.10 | 0.05-0.30 |

In a suitable container weigh out the formula amount of water of Phase A and with Lighting agitation, beginning at a minimum of 1,000 RPM and slowly sprinkling Natrosol into the vortex. As the viscosity thickens, increase the speed of the mixer to 1,500 to 2,500 RPM or until the full product forms a vortex. Addition of the Natrosol should take at about 15 to 20 minutes to complete. Begin heating to, and hold at 60° C., for 45-60 minutes, with mixing, until the product is clear and gelled. Add one ingredient at a time from the Surfactant Phase A with proper agitation, mixing between additions. In a separate container, weigh and combine all the materials of Phase B and begin to heat to 70° C. to 75° C. Combine the Phase B ingredients together using a homogenizer (starting at 2,500 RPM) and increasing as needed for at least 15 to 20 minutes until a uniform, non-grainy dispersion is achieved. Slowly add Phase B to Phase A, mixing until uniform. Heat Phase A/Phase B mixture to 70° C. to 75° C. Mix for approximately 30 minutes at temperature until completely uniform and creamy. Discontinue heating. Allow Phase A/Phase B mixture to cool to 40° C. to 45° C. with continuous lightning. Add preservative and essential oil. Mix well.

EXAMPLE 2

Aerosolized Liquid SPF Cleansing Composition

The composition according to Example 1 serves as a concentrate is combined with A46 propellant at a ratio of 96% concentrate to 4% propellant. The concentrate is added to an aluminum can to which a valve is crimped. Propellant is then charged into the crimped container at a pressure of 46 psig, +/−8 psi. When the actuator is engaged, the valve opens releasing the aerosolized SPF liquid composition. Upon application to the skin, the product is a shiny, flowable, tinted product which within seconds increases in volume and appears as a mousse.

EXAMPLE 3

SPF After Cleansing and Rinsing

A study to determine SPF before and after cleansing was performed over a three-day period. On the first day of the study, each subject received a series of measured UV doses from a xenon arc solar simulator to an unprotected site on the mid-back.

On the second day, the minimal erythema dose (MED) was determined as the lowest UV dose which produced mild erythema reaching the borders of the exposure site. Next, 50 $cm^2$ test areas were drawn on the backs of study participants. The body wash formulation of Example 1 was applied to separate 50 $cm^2$ areas as follows: First, the skin was wet with 10 ml of distilled water at 100° F. Then, 100 mg of the SPF liquid cleansing composition was applied by "spotting" the product across the test area. The products were then rubbed into the skin for 1 minute. In a separate, adjacent test, 50 $cm^2$ area on the subject's back, 100 mg of the formulation of Example 1 was applied and rubbed into the dry skin for 1 minute. 100 mg of an 8% homosalate (HMS) standard supplied by Cosmetech Laboratories (Fairfield, N.J.) was applied to a third 50 $cm^2$ area of skin, also by "spotting" across the test area and gently rubbing into skin. In order to determine SPF after cleansing, the first test area was rinsed with 20 ml of distilled water at 100° F. dispensed in a constant stream under the same pressure from a 20 ml syringe with the syringe tip placed about 10 cm from the skin surface over a period of 30 seconds and then allowed to dry for 15 minutes. The other two test areas were not rinsed. (In the test area that was not rinsed, the HMS standard had an expected SPF of 4.)

After the 15-minute drying period, UV doses ranging from 0.64 to 1.56 times the product of the MED and 6 were administered to the area protected by the SPF liquid cleansing composition. The irradiation source was a calibrated xenon arc lamp solar simulator with an 8 mm liquid light guide (Model 16S, Solar Light Company, Philadelphia) that has an output spectrum in compliance with the 2007 Colipa Guideline. UV doses ranging from 0.64 to 1.56 times the product of the MED and 4 were administered to the area protected by the HMS standard sunscreen. A series of UV doses were also administered to an unprotected area.

On the third day, the MED was determined for the protected sites (those to which the SPF cleansing compositions and the HMS standard had been applied) and the unprotected site. The SPF was calculated as the ratio of the MED for each protected site to the MED for the unprotected site.

When tested in accordance with the above-described methodology (i.e., after application to wet skin, rubbing-in, rinsing-off, and drying), the body wash formulation of Example 1 had an SPF of 15 without rinsing and a post-rinse SPF of 7.9.

EXAMPLE 4

Photostability

Photostability was evaluated according to the proposed methods of Stanfield. See, J W Stanfield, "In vitro techniques in sunscreen development" in N. Shaath (ed.), *Sunscreens: Regulations and Commercial Development* (3rd Ed. Boca Raton:Taylor & Francis, 2005); J W Stanfield, "Optimizing in vitro measurement of sunscreen protection" *SOFW Journal* Vol. 132, pp. 19-22 (July 2006). Measurements of applied and transmitted UV dose were made at appropriate time intervals. A least squares curve fit equation was computed for the UV transmittance curve, using the equation y=ax$\beta$, where y is the transmitted UV dose and x is the applied UV dose and $\beta$ is an index of Photostability. If $\beta$ is equal to 1 the relationship between the applied and transmitted doses is linear, and the sunscreen is considered photostable; if $\beta$ is substantially greater than 1, the transmitted UV dose increases with applied dose, and the sunscreen is considered photolabile.

Applied and transmitted UV was measured at 1 nm intervals form 290 to 400 nm using a calibrated spectroradiometer (Model OL 756, Optronic Laboratories, Orlando). PMMA Substrates were Helioplates® (HelioScreen, Marseilles). Transmission spectra were interpolated as necessary to obtain spectra corresponding to UV doses Dx, 17.6 J/cm2 and ⅔ the labeled SPF in MEDs. Successive measured transmission spectra and the source irradiance were used to compute x and y. Based on the above photostability equation, the body wash of Example 1 was determined to be photo-stable.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A method of leaving an SPF of at least about 6 on a skin after a cleansing process that is followed by rinsing wherein the cleansing process comprises the sequential steps of:
   (a) calculating the MED on a human subject by
      (i) delivering a series of measured UV doses from a xenon arc solar simulator to an unprotected 50 cm$^2$ site on the subject's mid-back;
      (ii) 24 hours after step (a)(i) determining the minimal erythemal dose (MED) as the lowest UV dose which produced mild erythema reaching the borders of the site; and
   (b) wetting a 50 cm$^2$ area of skin with 10 ml of distilled water at 100° F.;
   (c) applying 100 mg of a liquid cleansing composition to the 50 cm$^2$ area, wherein the cleansing composition consists of:
      (a) 4% to 10% of red petrolatum;
      (b) 1% to 10% of at least one surface-treated metal oxide pigment that blocks ultraviolet radiation in the wavelength range of from about 290 nm to about 400 nm;
      (c) at least one organic sunscreen agent having a log P of greater than 4.0 that blocks or absorbs ultraviolet radiation in the wavelength range of from about 290 nm to about 400 nm;
      (d) at least one lathering anionic surfactant;
      (e) at least one lathering non-ionic surfactant;
      (f) 0.5% to 3% of an alkyl silicone wherein the alkyl silicone conforms to the structure

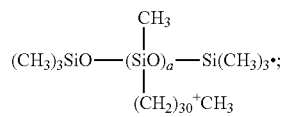

(g) a volatile cyclic silicone; and
   (h) 0.1% to 20.0% of melanin or a melanin precursor selected from the group consisting of L-dopa, tyrosine, tryptophan, and cysteine, and
   (i) iron oxide pigments
   (d) rubbing the 100 mg of the cleansing composition into the 50 cm$^2$ area of skin for one minute;
   (e) rinsing the 50 cm$^2$ area of skin with 20 ml distilled water at 100° F. for 30 seconds;
   (f) allowing the 50 cm$^2$ area of skin from which the cleansing composition was rinsed in step (e) to dry for fifteen minutes;
   (g) irradiating the 50 cm$^2$ area that was allowed to dry in step (f) with a dose of ultraviolet radiation from a xenon arc solar simulator UV ranging from 0.64 to 1.56 times the MED;
   (h) calculating the SPF as the ratio of Q to R where
      (i) Q is the MED for the 50 cm$^2$ area to which the cleansing product had been applied, rubbed in, rinsed off and allowed to dry in steps (b)-(f); and
      (ii) R is the MED for the unprotected 50 cm$^2$ site.

2. The method of claim 1 wherein the at least one surface-treated metal oxide pigment that blocks ultraviolet radiation in the wavelength of from about 290 nm to about 400 nm is selected from the group consisting of:
   (a) micronized zinc oxide surface-treated with an alkoxysilane;
   (b) micronized titanium dioxide surface-treated with alkoxysilane;
   (c) micronized titanium dioxide surface-treated with silica, alumina and dimethicone/methicone copolymer;
   (d) micronized titanium dioxide surface-treated with alumina and dimethicone/methicone copolymer;
   (e) micronized zinc oxide surface-treated with an alkoxycaprylylsilane;
   (f) micronized titanium dioxide surface-treated with an alkoxycaprylylsilane; and
   (g) mixtures thereof.

3. The method of claim 1 wherein the at least one organic sunscreen agent having a log P of greater than about 4.0 that blocks or absorbs ultraviolet radiation in the wavelength range of from about 290 nm to about 400 nm is a cyanodiphenylacrylate.

4. The method of claim 1 wherein the at least one lathering anionic surfactant having a log P of less than 2.5 is selected from the group consisting of sulfates, isethionates, taurates and sarcosinates, salts thereof, derivatives thereof and mixtures thereof.

5. The method of claim 1 wherein the at least one lathering anionic surfactant having a log P of less than 2.5 is
   (a) sodium laureth sulfate or
   (b) ammonium laureth sulfate in combination with decyl glucoside.

6. The method of claim 1 wherein the at least one lathering non-ionic surfactant having a log P of less than 2.5 is an alkoxylated alcohol.

7. The method of claim 6 wherein the alkoxylated alcohol is a polyoxyethylene alkyl ether.

8. The method of claim 7 wherein the polyoxyethylene alkyl ether is the polyethylene glycol ether of stearyl alcohol conforming to the structure $CH_3(CH_2)_{17}(OCH_2CH_2)_n OH$ where n has an average value of 21.

9. The method of claim 1 that leaves an SPF of at least about 8 on the skin after the cleansing process.

* * * * *